United States Patent
Farnum et al.

(10) Patent No.: US 10,196,988 B2
(45) Date of Patent: Feb. 5, 2019

(54) FUEL SYSTEM COKING SENSOR

(71) Applicants: Rolls-Royce Corporation, Indianapolis, IN (US); Rolls-Royce North American Technologies, Inc., Indianapolis, IN (US)

(72) Inventors: David Farnum, Indianapolis, IN (US); Douglas D. Dierksmeier, Franklin, IN (US); Ben Moloney, Avon, IN (US); Patrick C. Sweeney, Indianapolis, IN (US)

(73) Assignees: Rolls-Royce Corporation, Indianapolis, IN (US); Rolls-Royce North American Technologies, Inc., Indianapolis, IN (US)

( * ) Notice: Subject to any disclaimer, the term of this patent is extended or adjusted under 35 U.S.C. 154(b) by 421 days.

(21) Appl. No.: 15/171,579

(22) Filed: Jun. 2, 2016

(65) Prior Publication Data

US 2016/0356224 A1 Dec. 8, 2016

Related U.S. Application Data

(60) Provisional application No. 62/171,301, filed on Jun. 5, 2015.

(51) Int. Cl.
*F02C 7/30* (2006.01)
*F02C 7/22* (2006.01)
(Continued)

(52) U.S. Cl.
CPC ............ *F02C 7/30* (2013.01); *F02C 7/22* (2013.01); *F02C 9/28* (2013.01); *G01N 27/14* (2013.01);
(Continued)

(58) Field of Classification Search
CPC ...... F02C 7/30; F02C 9/28; F02C 7/22; G01N 27/14; G01N 21/8422; G01N 21/55; G01N 2021/945; Y02T 50/675; F05D 2260/607
(Continued)

(56) References Cited

U.S. PATENT DOCUMENTS 4,158,610 A * 6/1979 Bauer ................... C10B 43/00
201/1
4,209,490 A * 6/1980 Duncan ................ B01J 19/0026
196/110

(Continued)

FOREIGN PATENT DOCUMENTS

EP 2783160 A1 10/2014
EP 3101249 A1 * 12/2016 ............... F02C 7/30

OTHER PUBLICATIONS

European Search Report dated Nov. 11, 2016 related to European Application 16172953.8.

*Primary Examiner* — Jason Newton
(74) *Attorney, Agent, or Firm* — Fishman Stewart PLLC

(57) ABSTRACT

An improved system, apparatus and method may be configured for detecting coking in a gas turbine engine. The system may comprise one or more heatable collecting elements configured to be positioned in a fuel supply passage having an inlet and an outlet. The apparatus heatable collecting may be configured to generate heat at or over a fuel system temperature range to induce coking in at least one of the heatable collecting elements. The apparatus may also include a sensor configured to detect an indication of coking on the heatable collecting elements and, in response to the coking indication, communicate a coking condition signal to an engine control.

20 Claims, 3 Drawing Sheets

(51) Int. Cl.
  *G01N 27/14* (2006.01)
  *F02C 9/28* (2006.01)
  *G01N 21/94* (2006.01)
  *G01N 21/55* (2014.01)
  *G01N 21/84* (2006.01)

(52) U.S. Cl.
  CPC ........ *F05D 2260/607* (2013.01); *G01N 21/55* (2013.01); *G01N 21/8422* (2013.01); *G01N 2021/945* (2013.01); *Y02T 50/675* (2013.01)

(58) Field of Classification Search
  USPC .......................................................... 60/779
  See application file for complete search history.

(56) References Cited

U.S. PATENT DOCUMENTS

| | | | |
|---|---|---|---|
| 5,965,451 A * | 10/1999 | Plog | G01N 27/221 422/90 |
| 6,490,927 B2 * | 12/2002 | Braunling | G01N 17/04 73/597 |
| 6,602,471 B1 * | 8/2003 | Sato | F01N 3/0814 422/68.1 |
| 7,377,112 B2 | 5/2008 | Spadaccini et al. | |
| 7,450,235 B1 * | 11/2008 | Said | G01N 21/31 356/432 |
| 7,543,477 B2 * | 6/2009 | Berger | G01N 15/0656 73/23.33 |
| 7,819,009 B2 | 10/2010 | Borah et al. | |
| 8,347,828 B2 * | 1/2013 | Yoshida | G01N 33/2829 123/1 A |
| 8,387,400 B2 | 3/2013 | Goeke et al. | |
| 8,469,700 B2 * | 6/2013 | Peluso | G01N 17/00 431/13 |
| 8,499,620 B2 * | 8/2013 | Sako | F01D 21/10 73/64.41 |
| 8,676,436 B2 | 3/2014 | Raimarckers et al. | |
| 2004/0040550 A1 * | 3/2004 | Someno | F02D 37/02 123/704 |
| 2009/0207413 A1 * | 8/2009 | Carpenter | G01N 21/31 356/437 |
| 2010/0043528 A1 * | 2/2010 | Brothier | G01N 5/02 73/28.04 |
| 2012/0090381 A1 * | 4/2012 | Andersson | G01N 27/129 73/31.06 |
| 2012/0285402 A1 * | 11/2012 | Foster | F01D 17/02 123/41.12 |
| 2013/0019651 A1 * | 1/2013 | Sasaki | F02D 41/222 73/1.02 |
| 2013/0092124 A1 * | 4/2013 | Lorenz | F02D 41/008 123/305 |
| 2013/0122593 A1 * | 5/2013 | Wolf | G01N 17/04 436/6 |
| 2013/0199571 A1 * | 8/2013 | Wickham | B08B 7/0071 134/19 |
| 2013/0318948 A1 * | 12/2013 | Van Marion | F02D 41/1466 60/277 |
| 2014/0026636 A1 * | 1/2014 | Pastecki | G01N 33/222 73/23.2 |
| 2014/0294040 A1 | 10/2014 | Zhang et al. | |
| 2014/0302614 A1 * | 10/2014 | Porter | B01J 23/83 436/139 |
| 2014/0311953 A1 | 10/2014 | Chimenti et al. | |
| 2016/0018381 A1 * | 1/2016 | Potyrailo | G01N 27/026 324/633 |
| 2017/0081997 A1 * | 3/2017 | Potyrailo | G01N 33/2888 |
| 2017/0138876 A1 * | 5/2017 | Potyrailo | G01N 33/2888 |
| 2017/0138922 A1 * | 5/2017 | Potyrailo | G01N 33/2888 |
| 2017/0227425 A1 * | 8/2017 | Martucci | G01M 15/14 |
| 2017/0335770 A1 * | 11/2017 | Glahn | F02C 3/04 |

* cited by examiner

FUEL SYSTEM COKING SENSOR

CROSS-REFERENCE TO RELATED APPLICATIONS

This application is a non-provisional application claiming priority to U.S. Provisional Application No. 62/171,301 filed Jun. 5, 2015, which is hereby incorporated by reference in its entirety.

FIELD OF TECHNOLOGY

An improved system for a gas turbine engine, and more specifically, a fuel system having a coking sensor configured to detect an indication of coking including a build-up or accumulation of unwanted deposits such as carbon.

BACKGROUND

Gas turbine engines typically include a compressor, a fuel system, a combustor, and a turbine. The compressor compresses air drawn into the engine and delivers high pressure air to the combustor. The fuel system delivers fuel such as liquid hydrocarbon fuel to the combustor, where it is mixed with the high pressure air and is ignited. Products of a combustion reaction in the combustor are directed into the turbine where work is extracted to drive the compressor and, sometimes, an output shaft. More specifically, combustors in gas turbine engines provide an energy release that drives the turbine. This energy release takes the form of high temperature gases. The handling of these gases drives the overall performance of the engine.

Recent advancements in such a gas turbine engine may use the liquid hydrocarbon fuel to cool hotter portions of the engine. In the process of cooling, the fuel can be heated to temperatures above the thermal stability limit of fuel, thereby resulting in the formation of coking including gum, tar, and varnish deposits within the fuel system. An approach for preventing such deposits involves removing or reducing the dissolved oxygen normally found in untreated jet fuel as it flows into the engine. Insufficient oxygen removal may occur due to failure or miscalibration of the oxygen removal system. The safety and efficient operation of a robustly engineered "hot fuel" system requires a means to detect such failure by measuring either oxygen concentration directly or the formation of coke deposits caused by insufficient oxygen removal. Thus, detection of coking is crucial to the operation and maintenance of gas turbine engines operating with fuel temperatures above thermal stability limits.

Traditional systems for measuring the percentage of entrained oxygen in the liquid hydrocarbon fuels are unsuitable for aircraft applications due to their size and weight. Further, typical systems may require regular calibration and adjustment resulting in variable and unreliable data outputs. Moreover, traditional systems do not provide an indication of factors, other than oxygen, that influence fuel quality and contribute to the coking of engine surfaces Thus, there is a need for a system, apparatus, and method to detect coking in fuel systems, e.g., that operate above the fuel thermal stability limit and rely on an oxygen removal device to reduce accumulation of unwanted deposits such as carbon. Accordingly, the detection of coking by this method may facilitate a change in engine operating conditions to slow the coke deposition rate, or the timely maintenance of the engine fuel system for removal of unwanted deposits, thereby increasing engine efficiency and reliability.

BRIEF DESCRIPTION OF THE DRAWINGS

While the claims are not limited to a specific illustration, an appreciation of the various aspects is best gained through a discussion of various examples thereof. Referring now to the drawings, exemplary illustrations are shown in detail. Although the drawings represent the illustrations, the drawings are not necessarily to scale and certain features may be exaggerated to better illustrate and explain an innovative aspect of an example. Further, the exemplary illustrations described herein are not intended to be exhaustive or otherwise limiting or restricted to the precise form and configuration shown in the drawings and disclosed in the following detailed description. Exemplary illustrations are described in detail by referring to the drawings as follows:

Figure 1:
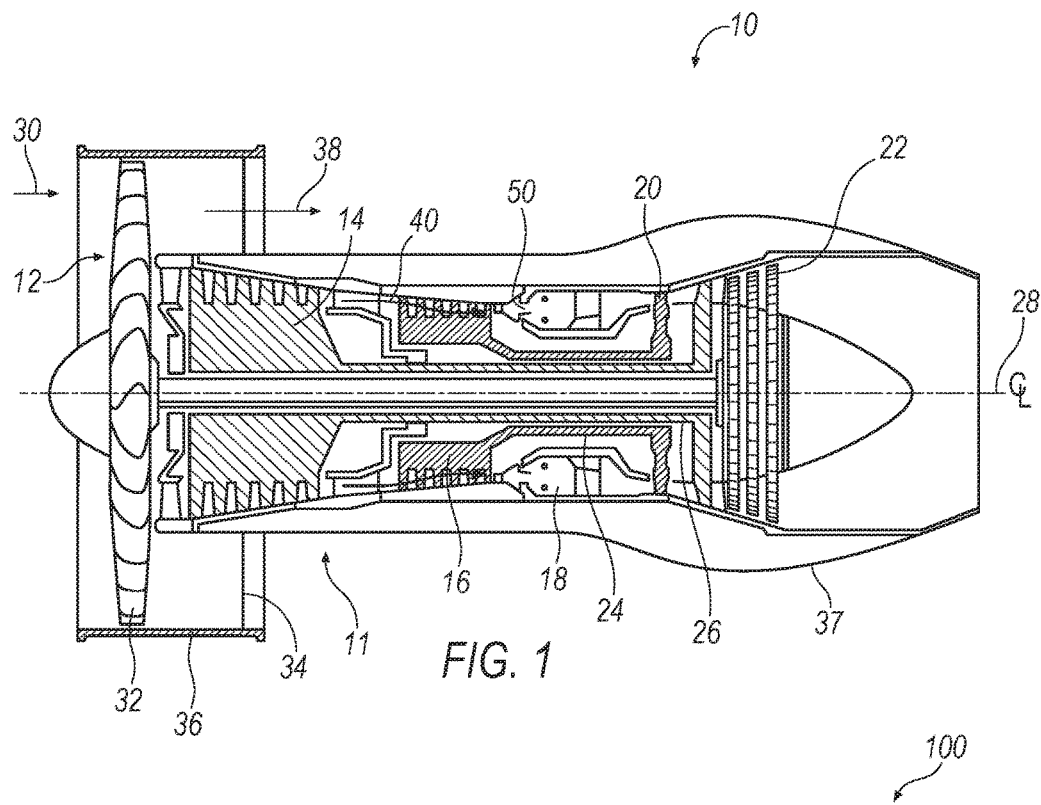
FIG. 1 illustrates an exemplary gas turbine engine.

For the purposes of promoting an understanding of the principles of the embodiments, reference will now be made to the embodiments illustrated in the drawings and specific language will be used to describe the same. It will nevertheless be understood that no limitation of the scope of the embodiments is thereby intended. Any alterations and further modifications in the described embodiments, and any further applications of the principles of the embodiments as described herein are contemplated as would normally occur to one skilled in the art to which the embodiment relates.

DETAILED DESCRIPTION

An exemplary coking sensor system may be configured to induce and detect an indication of coking upstream of higher or maximum temperature regions of the engine based on the downstream conditions. The higher or maximum temperature regions may operate at temperatures above the thermal stability limit of fuel (e.g., liquid hydrocarbon fuel), thereby producing coking in the engine fuel system at higher or maximum temperature regions of the engine. The higher or maximum temperature regions may include any heat source that may heat the fuel, e.g., any portion of the engine that may raise the fuel temperature above its thermal stability limit such as a heat exchanger, fuel cooled cooler, or another hotter portion of the engine. Fuel systems may include a fuel stabilization system to reduce or eliminate coking. A fuel system temperature sensor may be configured to measure a fuel system temperature range near or downstream of the heat source and provide a fuel system temperature signal to a coking sensor system upstream of the heat source. The coking sensor system may be configured to heat the upstream fuel to the fuel system temperature range, thereby inducing coking conditions upstream of the heat source that are comparable to the downstream coking conditions near or downstream of the heat source. By imparting heat at the fuel system temperature range, the coking sensor system may detect an indication of coking upstream of the heat source and, in response to the coking condition, provide a coking condition signal to the engine control, thereby providing a notification to the engine control and allowing the engine control to take appropriate actions with respect to the coking indication.

An exemplary coking sensor system may include one or more heatable collecting elements having one or more surfaces configured to induce coking. The heatable collecting elements may be configured to be positioned in a fuel supply passage having an inlet and an outlet. The heatable collecting elements may be configured to generate heat at or over a range of fuel system temperature, e.g., to induce coking with respect to the surfaces of the heatable collecting element. The heatable collecting elements may be made with the same or similar materials and surface finishes to those in the hotter portions of the fuel system, so as to replicate catalytic effects and induce coking upstream under comparable conditions to those downstream in the engine. The system may also include a sensor configured to detect an indication of coking (e.g., physical build-up or accumulation of deposits) with respect to at least one of the heatable collecting elements and, in response to the coking indication, communicate a coking condition signal to an engine control.

FIG. 1 illustrates a gas turbine engine 10, which includes a fan 12, a low pressure compressor 14, a high pressure compressor 16, a combustor 18, a high pressure turbine 20, and a low pressure turbine 22. The high pressure compressor 16 is connected to a first rotor shaft 24 while the low pressure compressor 14 is connected to a second rotor shaft 26. The shafts 24, 26 extend axially and are parallel to an engine centerline axis 28. Ambient air 30 enters the fan 12 and is directed across a fan rotor 32 in an annular fan bypass duct 34, which in part is circumscribed by nacelle 36. The bypass airflow 38 provides engine thrust while the primary gas stream 40 is directed to area 50 and into the combustor 18 and the high pressure turbine 20. The fan nacelle 36 is spaced radially outwardly from the core casing 37 to define an annular bypass duct 34 therebetween. During operation, the core engine 11 powers the fan 12 which pressurizes ambient air 30 to produce propulsion thrust in the fan air 38 bypassing the core engine 11 and discharged from the fan exhaust nozzle (not shown).

Figure 2:
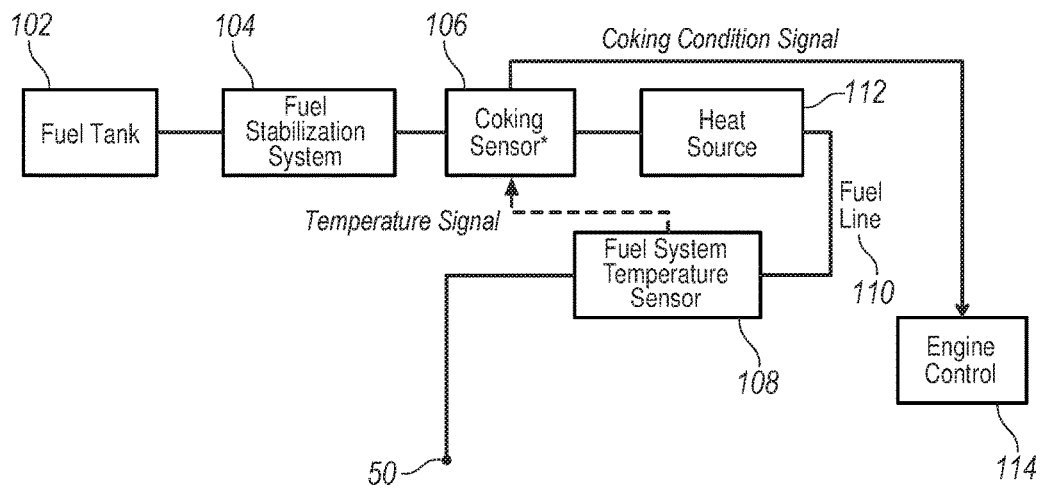
FIG. 2 illustrates an exemplary fuel system, for example, including a fuel tank, a fuel stabilization system, a coking sensor system, a heat source, a fuel system temperature sensor, and an engine control.

FIG. 2 illustrates a fuel system 100. Fuel system 100 may include a fuel tank 102, a fuel stabilization system 104, a coking sensor system 106, a fuel system temperature sensor 108, a fuel line 110, a heat source 112, and an engine control 114. The fuel stabilization system 104 may include a fuel treatment device configured to treat fuel and/or an oxygen removal device configured to remove oxygen from fuel. The coking sensor system 106 may be positioned downstream of the fuel stabilization system 104 and upstream or remote from heat source 112. Heat source 112 may include any portion of the engine 10 that may raise the fuel temperature above its thermal stability limit such as a heat exchanger, fuel cooled cooler, or a hotter portion of the engine 10. It is appreciated that the fuel cooled cooler may utilize air, oil, refrigerant, any other heat carrying fluid or material, or any combination thereof. Fuel from the fuel tank 102 may pass along the fuel stabilization system 104, coking sensor system 106, heat source 112 (e.g., heating the fuel), and the fuel system temperature sensor 108. The fuel system temperature sensor 108 may include a downstream sensor relative to coking sensor system 106, e.g., positioned remote from coking sensor system 106 and at one or more locations downstream of the coking sensor system 106 and near or downstream of heat source 112. The fuel system temperature sensor 108 may be configured to measure a fuel system temperature range (e.g., a temperature or a range of temperatures measured downstream of coking sensor system 106 near or downstream of a higher or maximum temperature region of engine 10) of fuel system 100 and communicate the fuel system temperature range to the coking sensor system 106. With the measured fuel system temperature range, the coking sensor system 106 may generate heat at or over the fuel system temperature range upstream of the heat source 112, thereby inducing coking on one or more heatable collecting elements 216 under similar conditions to that experienced by the surfaces of the engine 10 that are downstream of coking sensor system 106, e.g., near or downstream of a higher or maximum temperature region of engine 10. In response to detecting coking in the coking sensor system 106, the coking sensor system 106 may send a coking condition signal to the engine control 114, e.g., thereby providing a notification of coking with respect to the downstream surfaces of engine 10.

Figure 3:
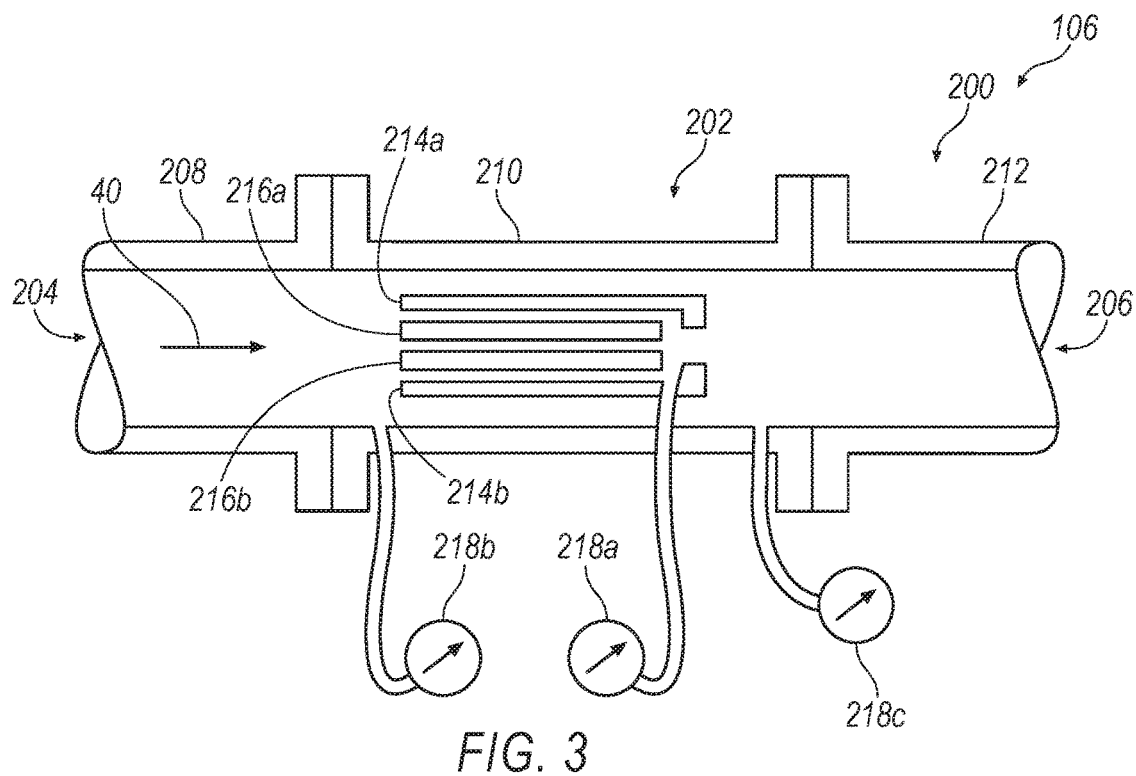
FIG. 3 illustrates an exemplary embodiment of a coking sensor system, for example, including one or more heatable collecting elements having surfaces configured to induce coking, and one or more pressure sensors.

FIG. 3 illustrates an exemplary embodiment of coking sensor system 106 including coking sensor system 200. System 200 may include a fuel line 202 having an inlet 204 and an outlet 206 forming a fuel passage, e.g., a fuel supply passage. The fuel line 202 may include an inlet portion 208 in fluid communication with the fuel stabilization system 104, a sensor portion 210 configured to detect coking, and an outlet portion 212 in fluid communication with the combustor 18. The sensor portion 210 may be fixedly or removeably attachable with respect to the inlet and outlet portions 208, 212, e.g., to facilitate access to or maintenance of sensor portion 210. The system 200 may include one or a plurality of heatable collecting elements 216, flow directing elements 214, and sensors 218.

The system 200 may be configured for measuring and detecting coking, e.g., thereby providing an advanced indication of impending coking downstream near a higher or maximum temperature region of engine 10. An exemplary sensor 218 may include an upstream sensor as part of system 200. Sensor 218 may include one or more pressure, optical, temperature, proximity, vibration, or impedance sensors or any combination thereof that are configured to measure a parameter or a parameter change related to any of pressure, reflectivity, emissivity, temperature, distance, thickness, normal or resonant frequency, mass, or impedance or conductance. The system 200 may be configured to measure and detect coking, e.g., thereby indicating near or downstream of a higher or maximum temperature region of engine 10. Alternatively or in addition, sensor 218 may be part of or integrated into heatable collecting element 216 and may be configured to provide heat and detect any of the parameters herein.

First and second heatable collecting elements 216a, 216b may be positioned in the fuel line 202, e.g., a fuel supply passage of engine 10. Flow directing element 214 may be disposed about the heatable collecting elements 216a, 216b and may be configured to direct fuel flow along heatable collecting elements 216a, 216b. The heatable collecting elements 216a, 216b may be configured to generate heat at or over the fuel system temperature range, e.g., to induce coking with respect to at least one of the first and second heatable collecting elements 216a, 216b. Coking of the first and second heatable collecting elements 216a, 216b, e.g., between and/or within flow directing elements 214, may increase the pressure differential between the inlet and outlet of flow directing elements 214a, 214b. As such, sensor 218 may be configured to measure an indication of coking (e.g., physical build-up or accumulation of deposits) on at least one of the heatable collecting elements 216a, 216b by measuring the pressure differential between sensor 218a and 218b and, in response to the coking indication, communicate a coking condition signal to an engine control 114. In addition, the coking sensor system 106 may be positioned in a primary flow area that receives a full fuel flow or a bypass flow area that receives a partial fuel flow, e.g., to reduce the cooling provided by the fuel flow to the one or more heatable elements 216 thereby reducing the power required to heat the one or more heatable elements 216.

One or more heatable collecting elements 216 may be temperature-controlled and may include one or more surfaces (e.g., first and second surfaces) that may be heated to induce coking formation thereon. Heatable collecting element 216 may be configured to generate heat to provide surface temperatures similar to those downstream of the coking sensor system 106, e.g., near or downstream of a higher or maximum temperature region of engine 10. For example, heatable collecting element 216 may be configured to convert electricity into heat through resistive heating. One or more heatable collecting elements 216 may be configured as a wire or plate, which may be inserted into a fuel line 110 a fuel system, e.g., a fuel supply line 202 of a "hot fuel" system.

Heatable collecting element 216 may be configured to facilitate the detection of the onset of coking, e.g., by inducing the heat currently being experienced near or downstream of a higher or maximum temperature region of engine 10. The heatable collecting element 216 may be heated to a surface temperature that the flowing fuel is likely to encounter further downstream in the engine 10. The heatable collecting element 216 may generate a surface temperature at a predefined heatable collecting set point that may be adjustable, e.g., in response to the fuel system temperature sensor 108 or temperatures measured during engine testing or startup. The heatable collecting element 216 may include any material and surface texture comparable to coke-prone surfaces of the "hot fuel" system, e.g., downstream of the coking sensor system 106. Thus, the system may be configured to detect the onset of coking upstream of the higher or maximum temperature regions to preserve the engine surfaces downstream of the coking sensor system 106, e.g., a fuel nozzle of engine 10. Thus, one or more heatable collecting elements may generate heat at or over the fuel system temperature range, thereby inducing coking on one or more heatable collecting elements 216 under similar conditions to that of the engine surfaces downstream of coking sensor system 106, e.g., near or downstream of a higher or maximum temperature region of engine 10.

Sensors 218 may be configured to detect an indication of coking (e.g., physical build-up or accumulation of deposits) in response to measured parameter or parameter change such as an increase or decrease relative to a coking threshold, e.g., predefined parameter or range based on measurements taken prior to or during the start of engine operation to provide a baseline for changes during operation. With further reference to FIG. 3, system 200 may include sensor 218. The sensor 218 may include an inlet pressure sensor 218b configured to measure an inlet static pressure (Pi) with respect to the inlet 204, an element pressure sensor 218a configured to measure a sensor static pressure (Ps) with respect to at least one of the first and second heatable collecting elements 216a, 216b, and an outlet pressure sensor 218c (Po) configured to measure an outlet static pressure with respect to the outlet 206. Sensors 218 are configured to detect coking in response to a measured change relative to a baseline or threshold pressure, e.g., predefined to indicate coking. For example, coking may be detected according to the following formula:

$$\frac{Ps - Pi}{Po - Pi} \text{ measured} > \frac{Ps - Pi}{P_o - P_i} \text{baseline}$$

Thus, sensor 218 may detect coking based on the relative pressure change.

Figure 4:
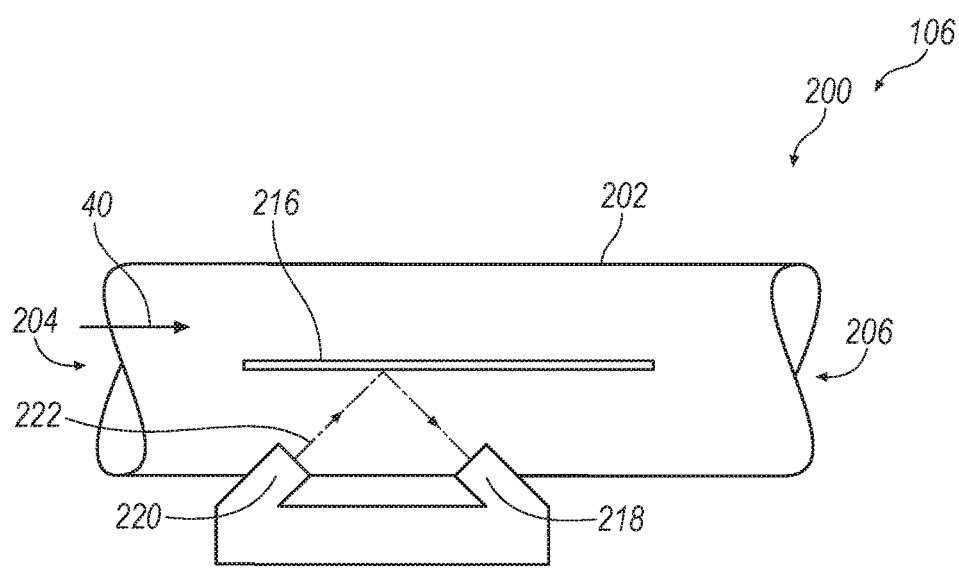
FIG. 4 illustrates another exemplary embodiment of a coking sensor system, for example, including one or more heatable collecting elements having surfaces configured to induce coking, and an optical sensor.

FIG. 4 illustrates another exemplary embodiment of a coking sensor system 200 including sensor 218, e.g., one or more optical sensors. The sensor 218 may be in communication with light source 220. Light source 220 may direct light beam toward and at an angle with respect to at least one heatable collecting element 216. The heatable collecting element 216 may reflect at least a portion of beam 222 to sensor 218. The heatable collecting element 216 may generate heat at or over the fuel system temperature range, e.g., thereby inducing coking on the heatable collecting element 216. Coking on the heatable collecting element 216 may change the reflectivity or emissivity of its surface. Sensor 218 may measure the changes in beam 222 in response to the change in the surface of heatable collecting element 216 with respect to the coking threshold, thereby detecting coking at coking sensor system 200, e.g., to indicate coking near or downstream of a higher or maximum temperature region of engine 10. Accordingly, sensor 218 may detect coking based on the reflectivity or emissivity change.

Figure 5:
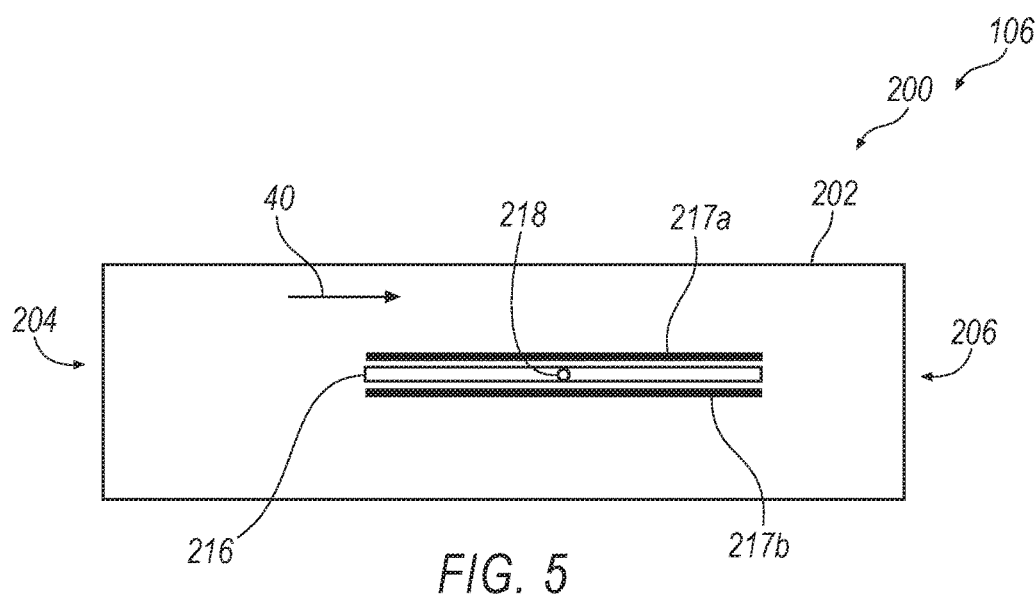
FIG. 5 illustrates another exemplary embodiment of a coking sensor system, for example, including one or more heatable collecting elements having surfaces configured to induce coking, and a temperature sensor.

FIG. 5 illustrates another exemplary embodiment of a coking sensor system including sensor 218, e.g., a temperature sensor. The sensor 218 may be embedded in or disposed on one or more heatable collecting elements 216. The heatable collecting element 216 may generate heat at or over the fuel system temperature range, e.g., thereby inducing coking on the heatable collecting element 216. Coking 217a, 217b may build on the surfaces of the heatable collecting element 216, e.g., thereby insulating the heatable collecting element 216 from fuel passing through fuel line 202. The sensor 218 may measure the relative temperature increase with respect to the coking threshold, thereby detecting coking at coking sensor system 200, e.g., to indicate coking near or downstream of a higher or maximum temperature region of engine 10. As a result, sensor 218 may detect coking based on the relative temperature change.

Figure 6:
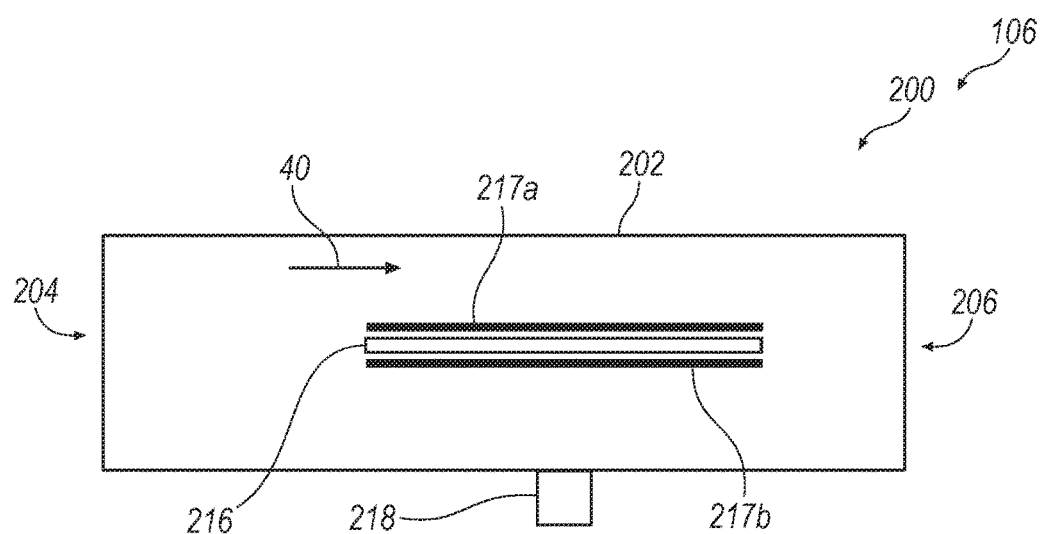
FIG. 6 illustrates another exemplary embodiment of a coking sensor system, for example, including one or more heatable collecting elements having surfaces configured to induce coking, and a proximity sensor.

FIG. 6 illustrates another exemplary embodiment of a coking sensor system including sensor 218, e.g., a proximity sensor such as a laser proximity sensor. The sensor 218 may be embedded in or disposed on the fuel supply passage of fuel line 202. The heatable collecting element 216 may generate heat at or over the fuel system temperature range, e.g., thereby inducing coking 217a, 217b on the surfaces of the collecting element 216. Coking may build on the heatable collecting surfaces 216, e.g., thereby increasing the thickness of and reducing the distance between the collecting surface 216 and sensor 218. Alternatively or in addition, one or more additional sensors 218 may be positioned at other locations along the fuel line 202, e.g., a second sensor 218 on the opposite side of fuel line 202 and to measure coke building on opposite surface of heatable collecting element 216. Thus, a first parameter may be measured on a first surface of heatable collecting surface 216a and a second parameter may be measured on a second surface of heatable collecting surface 216b, which may be used for calibration of system 200 or redundant measurements to confirm the accuracy of system 200. The sensor 218 may measure the distance decrease with respect to the coking threshold, thereby detecting coking at coking sensor system 200, e.g., to indicate coking near or downstream of a higher or maximum temperature region of engine 10. Accordingly, sensor 218 may detect coking based on the distance change.

Figure 7:
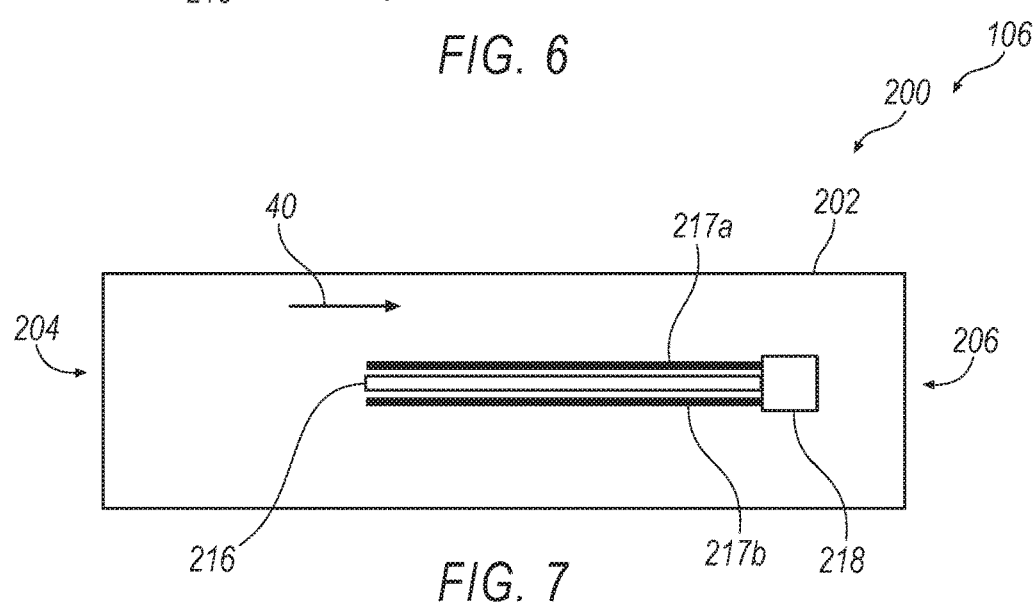
FIG. 7 illustrates another exemplary embodiment of a coking sensor system, for example, including one or more heatable collecting elements having surfaces configured to induce coking, and a vibration sensor.

FIG. 7 illustrates another exemplary embodiment of a coking sensor system including sensor 218, e.g., a vibration sensor such as an accelerometer or transducer. The sensor 218 may be positioned relative to at least one of the first and second heatable collecting elements 216a, 216b. The heatable collecting element 216 may generate heat at or over the fuel system temperature range, e.g., thereby inducing coking on the heatable collecting element 216. Coking 217a, 217b may build on the heatable collecting surfaces of 216, e.g., thereby increasing the mass of the collecting surfaces 216a, 216b and changing the natural or resonant frequency of the heatable collecting surfaces 216a, 216b in response to vibrational forces imparted by the fuel passing along fuel line 202 and over heatable collecting element 216. The sensor 218 may measure the relative frequency change with respect to the coking threshold, thereby detecting coking at the coking sensor system 200, e.g., to indicate coking near or downstream of a higher or maximum temperature region of engine 10. As a result, sensor 218 may detect coking based on the vibrational change.

Methods of operation are also contemplated. An exemplary method may include providing at least one heatable collecting element 216 having first and second surfaces. The method may further comprise measuring a fuel system temperature range downstream of the at least one heatable collecting element 216 using a downstream sensor 108, heating the at least one heatable collecting element 216 to approximately the fuel system temperature range, detecting an indication of coking on at least one of the first and second surfaces using an upstream sensor 218, and communicating a coking condition signal to the engine control 114.

In addition, methods of self-cleaning are also contemplated, e.g., after coking is detected and/or before the next operation of the engine 10. Air may be passed through the system 200 instead of fuel while the heatable collecting elements 116 are heated. The heatable collecting elements 116 may heat the coking deposits to a temperature sufficient to burn-off the carbon deposits. Thus, system 200 may be configured to perform self-cleaning.

The foregoing may provide a number of advantages. The coking sensor system 106 may provide improved accuracy over traditional systems. For example, the coking sensor system 106 may more directly measure the pressure, optical, temperature, proximity/thickness, and vibrational changes of the heatable collecting and/or collecting elements under comparable conditions to engine surfaces in higher or maximum temperature regions of the engine 10. Further, the coking sensor system 106 may directly focus on the detection of coking instead of tangential parameters such as fuel composition, thereby further enhancing accuracy over typical systems. Moreover, the coking sensor system 106 may be positioned in an upstream location that may be more easily cleaned or maintained, more easily accessed in the event of repair, removal, or replacement, and more benign or thermally tolerable to sensors 218, e.g., remote from the higher or maximum temperature regions of the engine 10. In addition, coking sensor system 106 may provide coking detection for fuel systems such as hot fuel systems and may be used to determine the effectiveness of oxygen removal systems.

The exemplary embodiments herein may be used in conjunction with any system of any vehicle including any engine system thereof. Merely as examples, embodiments of the present disclosure may include or be used in conjunction with any of the systems and methods disclosed in the cross-referenced disclosures mentioned above, which have been incorporated herein.

It will be appreciated that the aforementioned method and devices may be modified to have some components and steps removed, or may have additional components and steps added, all of which are deemed to be within the spirit of the present disclosure. Even though the present disclosure has been described in detail with reference to specific embodiments, it will be appreciated that the various modifications and changes can be made to these embodiments without departing from the scope of the present disclosure as set forth in the claims. The specification and the drawings are to be regarded as an illustrative thought instead of merely restrictive thought.

What is claimed is:

1. A coking sensor system for use in a gas turbine engine, comprising:
   at least one heatable collecting element having first and second surfaces, the at least one heatable collecting element being configured to be positioned in a fuel supply passage having an inlet and an outlet, the at least one heatable collecting element being configured to generate heat at or over a fuel system temperature range to induce coking on at least one of the first and second surfaces, and
   a sensor configured to detect an indication of coking on the at least one heatable collecting element and, in response to the coking indication, communicate a coking condition signal to an engine control.

2. The system of claim 1, wherein the sensor includes an inlet pressure sensor positioned with respect to the inlet, an element pressure sensor positioned with respect to the at least one heatable collecting element, and an outlet pressure sensor positioned with respect to the outlet.

3. The system of claim 2, wherein the sensor is configured to detect the coking indication based on a relative pressure increase of the element pressure sensor relative to the inlet and outlet pressure sensors.

4. The system of claim 1, wherein the sensor includes an optical sensor in communication with a light source.

5. The system of claim 1, wherein the sensor includes a temperature sensor disposed in communication with the at least one heatable collecting element.

6. The system of claim 1, wherein the sensor includes a proximity sensor positioned relative to the fuel supply passage.

7. The system of claim 1, wherein the sensor includes a vibration sensor positioned relative to the at least one heatable collecting element.

8. A method for operation of a coking detection system for a gas turbine engine, comprising;
   providing at least one heatable collecting element having first and second surfaces, the at least one heatable collecting element being configured to be positioned in a fuel supply passage having an inlet and an outlet;

measuring a fuel system temperature range downstream of the at least one heatable collecting element using a downstream sensor;

heating the at least one heatable collecting element to approximately the fuel system temperature range;

detecting an indication of coking on at least one of the first and second surfaces using an upstream sensor; and communicating, in response to the coking indication, a coking condition signal to an engine control.

9. The method of claim 8, wherein the upstream sensor includes an inlet pressure sensor positioned with respect to the inlet, an element pressure sensor positioned with respect to the at least one heatable collecting element, and an outlet pressure sensor positioned with respect to the outlet.

10. The method of claim 9, wherein the upstream sensor is configured to detect the coking indication based on a relative pressure increase of the element pressure sensor relative to the inlet and outlet pressure sensors.

11. The method of claim 8, wherein the upstream sensor includes an optical sensor in communication with a light source.

12. The method of claim 8, wherein the upstream sensor includes a temperature sensor disposed in the at least one heatable collecting element.

13. The method of claim 8, wherein the upstream sensor includes a proximity sensor positioned relative to the fuel supply passage.

14. A gas turbine engine system with coking detection, comprising:

a compressor;

a combustor;

a fuel system having a fuel supply passage connecting the compressor and the combustor, the fuel system having a coking sensor system including at least one heatable collecting element having first and second surfaces and being configured to be positioned in the fuel supply passage having an inlet and an outlet, the at least one heatable collecting element being configured to generate heat at or over a fuel system temperature range to induce coking with respect to at least one of the first and second surfaces, and a sensor configured to detect an indication of coking with respect to at least one of the first and second collecting elements and, in response to the coking indication, communicate a coking condition signal to an engine control.

15. The system of claim 14, wherein the sensor includes an inlet pressure sensor positioned with respect to the inlet, an element pressure sensor positioned with respect to the at least one heatable collecting element, and an outlet pressure sensor positioned with respect to the outlet.

16. The system of claim 15, wherein the sensor is configured to detect the coking indication based on a relative pressure increase of the element pressure sensor relative to the inlet and outlet pressure sensors.

17. The system of claim 14, wherein the sensor includes an optical sensor in communication with a light source.

18. The system of claim 14, wherein the sensor includes a temperature sensor disposed in the at least one heatable collecting element.

19. The system of claim 14, wherein the sensor includes a proximity sensor positioned relative to the fuel supply passage.

20. The system of claim 14, wherein the sensor includes a vibration sensor positioned relative to the at least one heatable collecting element.

* * * * *